US011458018B2

(12) United States Patent
Dekel et al.

(10) Patent No.: US 11,458,018 B2
(45) Date of Patent: Oct. 4, 2022

(54) JOINT SPACERS

(71) Applicant: Stryker European Operations Limited, Carrigtwohill (IE)

(72) Inventors: Assaf Dekel, Or Yehuda (IL); Idan Tobis, Caesarea (IL); Ruth Icekson, Caesarea (IL)

(73) Assignee: Stryker European Operations Limited

( * ) Notice: Subject to any disclaimer, the term of this patent is extended or adjusted under 35 U.S.C. 154(b) by 0 days.

(21) Appl. No.: 16/977,356

(22) PCT Filed: Jan. 28, 2019

(86) PCT No.: PCT/IB2019/050683
§ 371 (c)(1),
(2) Date: Sep. 1, 2020

(87) PCT Pub. No.: WO2019/171181
PCT Pub. Date: Sep. 12, 2019

(65) Prior Publication Data
US 2021/0052391 A1 Feb. 25, 2021

Related U.S. Application Data

(60) Provisional application No. 62/638,394, filed on Mar. 5, 2018.

(51) Int. Cl.
*A61F 2/30* (2006.01)
*A61F 2/40* (2006.01)
*A61F 2/46* (2006.01)

(52) U.S. Cl.
CPC ............ *A61F 2/30721* (2013.01); *A61F 2/40* (2013.01); *A61F 2002/30032* (2013.01);
(Continued)

(58) Field of Classification Search
CPC .......... A61F 2/40; A61F 2/44; A61F 2/30721; A61F 2/30723; A61F 2/30728;
(Continued)

(56) References Cited

U.S. PATENT DOCUMENTS 6,113,640 A  9/2000 Tormala et al.
7,258,700 B2 * 8/2007 Lambrecht ............ A61B 17/70
128/898
(Continued)

OTHER PUBLICATIONS

International Search Report including the Written Opinion for Application No. PCT/IB2019/050683 dated Sep. 30, 2019, 13 pages.

*Primary Examiner* — Brian A Dukert
(74) *Attorney, Agent, or Firm* — Lerner, David, Littenberg, Krumholz & Mentlik, LLP

(57) ABSTRACT

An apparatus including a joint spacer for treatment of a joint of a human subject. The joint spacer includes a bioresorbable stent having compressed and expanded configurations and a covering that covers an external surface of the stent. The joint spacer is configured to be inserted into a space of the joint, and is shaped, when the bioresorbable stent is in the expanded configuration, to provide mechanical support to the joint until the bioresorbable stent resorbs into a body of the subject. Treating a joint of a human subject includes inserting a joint spacer into a space of the joint while a bioresorbable stent of the joint spacer is in a compressed configuration, and transitioning the bioresorbable stent to an expanded configuration within the joint, such that the joint spacer provides mechanical support to the joint until the bioresorbable stent resorbs into a body of the subject.

17 Claims, 13 Drawing Sheets

(52) U.S. Cl.
CPC ............... *A61F 2002/30062* (2013.01); *A61F 2002/3093* (2013.01); *A61F 2002/30153* (2013.01); *A61F 2002/30228* (2013.01); *A61F 2002/30579* (2013.01); *A61F 2002/30754* (2013.01); *A61F 2002/30912* (2013.01); *A61F 2002/4615* (2013.01)

(58) Field of Classification Search
CPC .. A61F 2002/30061; A61F 2002/30228; A61F 2002/30579; A61F 2002/30754; A61F 2002/30912; A61F 2002/4615; A61F 2002/30733; A61F 2002/30062
See application file for complete search history.

(56) References Cited

U.S. PATENT DOCUMENTS

| | | | | |
|---|---|---|---|---|
| 8,298,289 | B2* | 10/2012 | White | A61F 2/30721 623/21.11 |
| 8,894,713 | B2* | 11/2014 | Shohat | A61F 2/4081 623/19.13 |
| 2004/0167625 | A1* | 8/2004 | Beyar | A61B 17/7266 623/11.11 |
| 2006/0085075 | A1 | 4/2006 | McLeer | |
| 2007/0093899 | A1* | 4/2007 | Dutoit | A61B 17/7097 623/17.11 |
| 2011/0295379 | A1* | 12/2011 | Shohat | A61F 2/4241 623/21.11 |
| 2013/0116794 | A1* | 5/2013 | Shohat | A61F 2/30756 623/19.11 |
| 2018/0256217 | A1 | 9/2018 | Dekel et al. | |

\* cited by examiner

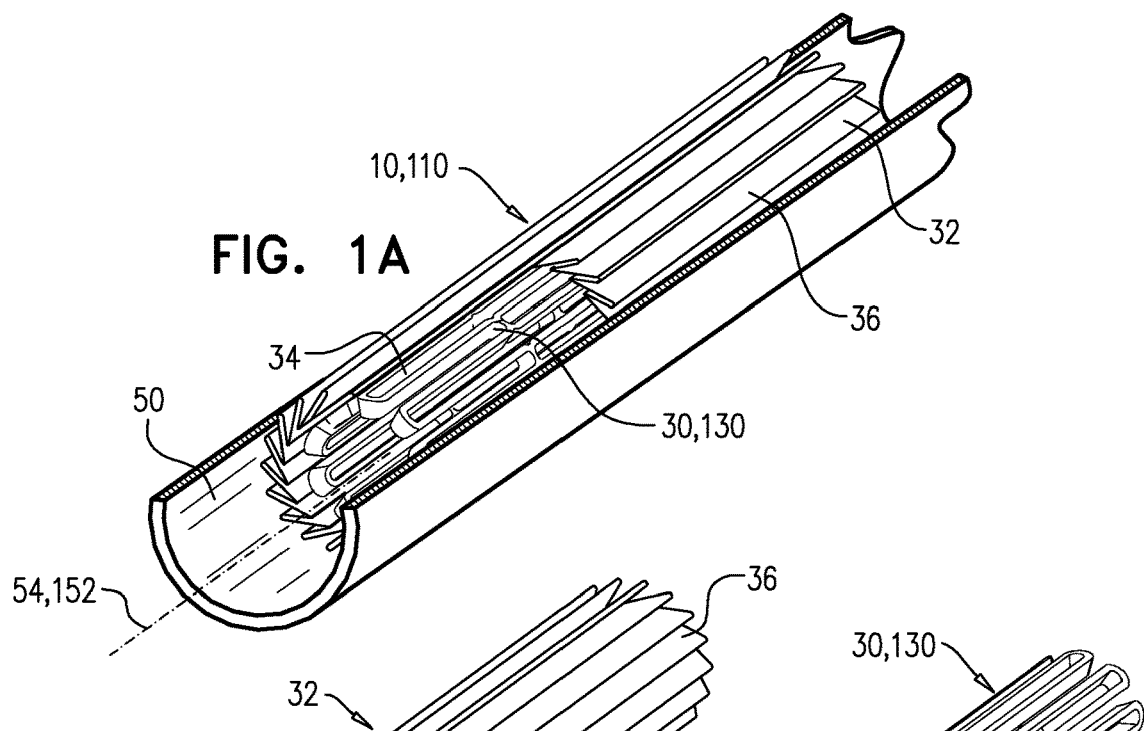
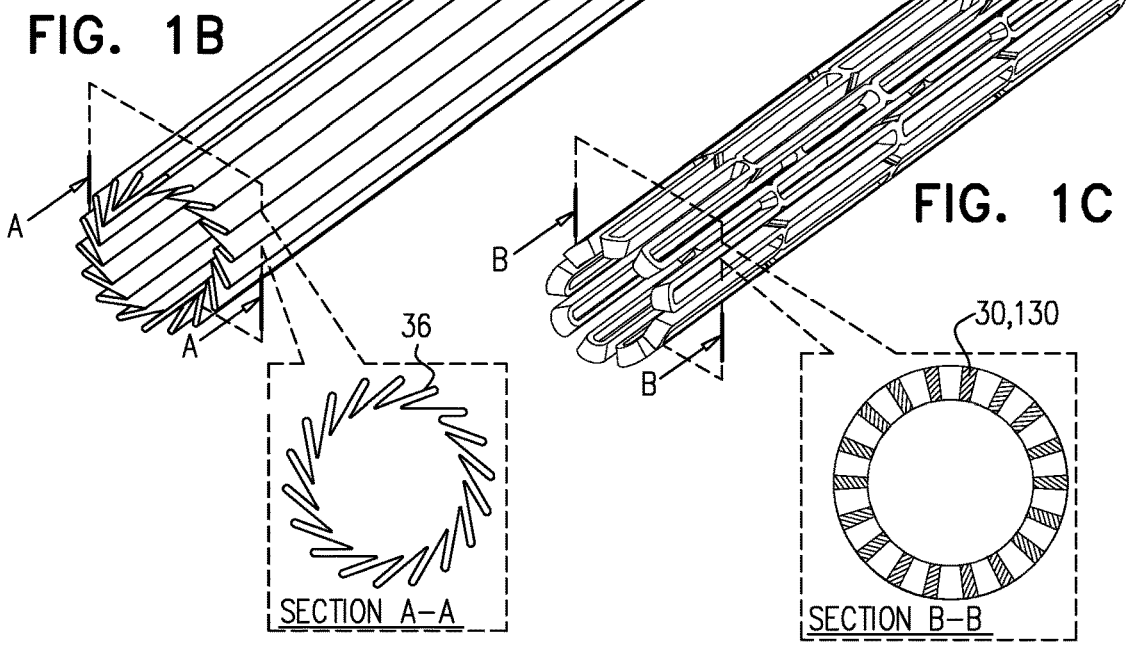
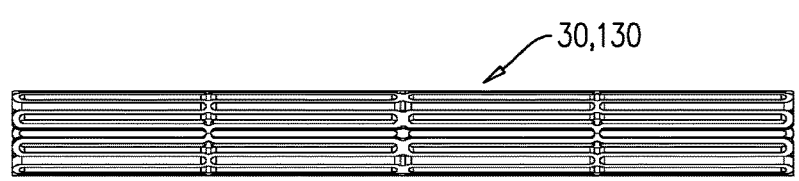

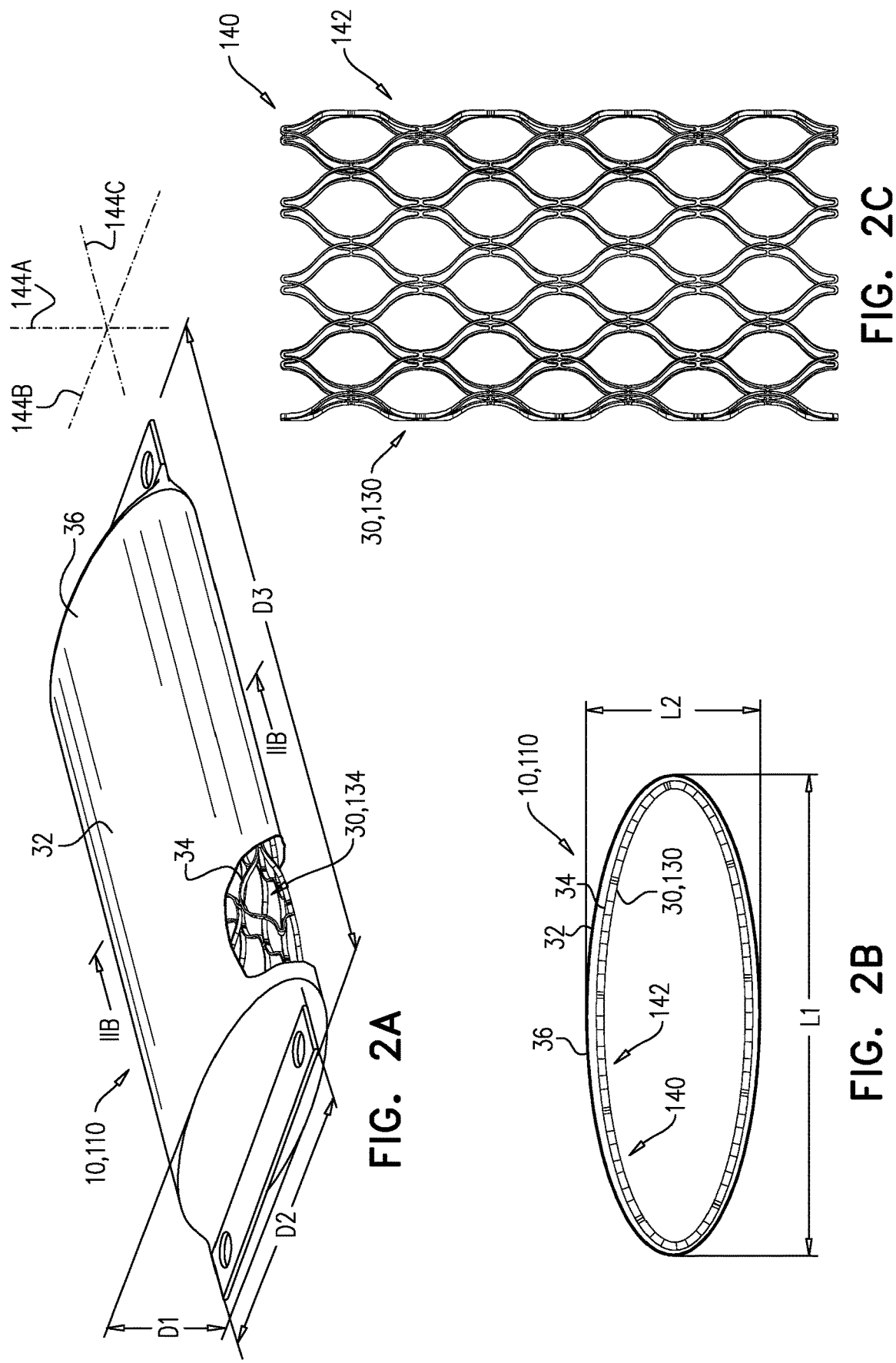

JOINT SPACERS

CROSS-REFERENCE TO RELATED APPLICATIONS

The present application is a national phase entry under 35 U.S.C. § 371 of International Application No. PCT/IB2019/050683, filed Jan. 28, 2019, published in English as WO 2019/171181 A2, which claims priority from U.S. Provisional Application No. 62/638,394 filed on Mar. 5, 2018, all of which are incorporated by reference herein in their entirety.

TECHNICAL FIELD

The present invention relates generally to techniques for treating joints, and specifically to joint spacers.

BACKGROUND

Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues.

SUMMARY

Embodiments of the present disclosure provide a joint spacer for treatment of a joint of a human subject. The joint spacer includes a bioresorbable stent having compressed and expanded configurations, and a covering that covers an external surface of the stent. The joint spacer is configured to be inserted into a space of the joint, and is shaped, when the bioresorbable stent is in the expanded configuration, to provide mechanical support to the joint until the bioresorbable stent resorbs into a body of the subject while new tissue is remodeled. For some applications, the joint spacer may simulate at the size or shape of a natural bursa.

For some applications, the joint spacer is a subacromial spacer and the joint is a shoulder joint, and the subacromial spacer is shaped and sized so as to be insertable into a subacromial space of the shoulder joint to provide support to the shoulder joint until the bioresorbable stent resorbs into the body of the subject. For example, the subacromial spacer may be used for treating a rotator cuff injury. For other applications, the joint spacer is a glenohumeral spacer and the joint is a glenohumeral joint, and the glenohumeral spacer is shaped and sized so as to be insertable into the glenohumeral joint to provide support to the glenohumeral joint until the bioresorbable stent resorbs into the body of the subject.

Typically, the bioresorbable stent is configured to resorb into the body of the subject between 3 and 36 months after placement in the joint. This period of time may allow soft tissue to grow into the space defined and structurally supported by the joint spacer while the bioresorbable stent resorbs into the body, thereby providing long-term treatment to the joint without the long-term presence of a prosthetic implant.

For some applications, the covering is shaped as a pouch within which the bioresorbable stent is disposed, at least immediately upon placement within the joint.

For some applications, the covering is bioresorbable. For some applications, the bioresorbable covering is configured to resorb into the body of the subject between 3 and 36 months after placement in the joint. For some applications, the bioresorbable stent and the bioresorbable covering are configured such that the bioresorbable stent resorbs into the body of the subject before the bioresorbable covering resorbs into the body of the subject. As a result, the bioresorbable covering may protect the joint from direct exposure to the bioresorbable stent until the bioresorbable stent resorbs.

For some applications, the covering is configured to promote tissue growth thereon and/or therethrough, into the space defined by the spacer. For example, the covering may be coated with a tissue-growth-promoting material.

For some applications, the bioresorbable stent is shaped as a partially-flattened tube when the joint spacer is unconstrained and the bioresorbable stent is in the expanded configuration. For some applications, when the joint spacer is unconstrained and the bioresorbable stent is in the expanded configuration, the bioresorbable stent is shaped generally as a cylinder, such as an elliptical or oval cylinder.

For other applications, the bioresorbable stent includes a plurality of wires arranged as a braided mesh. For some applications, the bioresorbable stent is shaped generally as an ovoid (e.g., an ellipsoid or a spheroid) when the joint spacer is unconstrained and the bioresorbable stent is in the expanded configuration.

There is therefore provided an apparatus including a joint spacer for treatment of a joint of a human subject, the joint spacer including:

a bioresorbable stent having compressed and expanded configurations; and a covering that covers an external surface of the stent, wherein the joint spacer is configured to be inserted into a space of the joint, and is shaped, when the bioresorbable stent is in the expanded configuration, to provide mechanical support to the joint until the bioresorbable stent resorbs into a body of the subject.

For some applications, the covering is fluid-permeable and blood-permeable. For some applications, the covering is tissue-permeable.

For some applications, the joint spacer is not shaped so as to allow directional blood flow therethrough, at least immediately upon placement within the joint. For some applications, the covering does not define a tubular lumen therethrough when the joint spacer is unconstrained and the bioresorbable stent is in the expanded configuration, at least immediately upon placement within the joint. For some applications, the bioresorbable stent does not include any circular cylindrical portions when the joint spacer is unconstrained and the bioresorbable stent is in the expanded configuration, at least immediately upon placement within the joint.

For some applications, the bioresorbable stent includes a metal selected from the group of metals consisting of: magnesium, a magnesium alloy, calcium, a calcium alloy, iron, and an iron alloy other than steel.

For some applications, the covering is sachet-shaped at least immediately upon placement within the joint.

For some applications, the covering is rectangular at least immediately upon placement within the joint.

For some applications, the covering is square at least immediately upon placement within the joint.

For some applications, the covering is shaped as a pouch within which the bioresorbable stent is disposed, at least immediately upon placement within the joint. For some applications, the pouch is shaped so as to define a closed space therewithin at least immediately upon placement within the joint. For some applications, the pouch is not shaped so as to define any openings that have a cross-sectional area greater than 3 mm² at least immediately upon placement within the joint.

For some applications, the bioresorbable stent is shaped as a partially-flattened tube when the joint spacer is unconstrained and the bioresorbable stent is in the expanded configuration.

For some applications, wherein, when the joint spacer is unconstrained and the bioresorbable stent is in the expanded configuration, the bioresorbable stent is shaped generally as a cylinder selected from the group consisting of: an elliptical cylinder and an oval cylinder. For some applications, the bioresorbable stent is shaped generally as the elliptical cylinder, and the length of the major axis of the elliptical cylinder equals at least 200% of the length of the minor axis of the elliptical cylinder when the joint spacer is unconstrained and the bioresorbable stent is in the expanded configuration. For some applications, the bioresorbable stent is shaped generally as the oval cylinder, and the distance between the axes of the oval cylinder equals at least 200% of the radii of the oval cylinder when the joint spacer is unconstrained and the bioresorbable stent is in the expanded configuration.

For some applications, the apparatus further includes a delivery tube, in which the joint spacer is removably disposed for delivery in a radially-compressed configuration with a central longitudinal axis thereof parallel to a longitudinal axis of the delivery tube.

For some applications, the bioresorbable stent includes a plurality of wires arranged as a braided mesh. For some applications, the bioresorbable stent is shaped generally as an ovoid when the joint spacer is unconstrained and the bioresorbable stent is in the expanded configuration. For some applications, the bioresorbable stent is shaped generally as an ellipsoid when the joint spacer is unconstrained and the bioresorbable stent is in the expanded configuration. For some applications, the bioresorbable stent is shaped generally as a spheroid when the joint spacer is unconstrained and the bioresorbable stent is in the expanded configuration. For some applications, the bioresorbable stent is shaped generally as an oblate spheroid when the joint spacer is unconstrained and the bioresorbable stent is in the expanded configuration.

For some applications, the bioresorbable stent includes a plurality of wires arranged as a braided mesh.

For some applications, the wires cross one another within 3 mm of a first pole of the oblate spheroid and within 3 mm of a second pole of the oblate spheroid when the joint spacer is unconstrained and the bioresorbable stent is in the expanded configuration.

For some applications, the length of each of the semi-axes of the oblate spheroid equals at least 200% of the length of the symmetry axis of the oblate spheroid when the joint spacer is unconstrained and the bioresorbable stent is in the expanded configuration.

For some applications, the apparatus further includes a delivery tube, in which the joint spacer is removably disposed for delivery in a compressed axially-elongated configuration with a central longitudinal axis thereof parallel to a central longitudinal axis of the delivery tube. For some applications, the apparatus further includes a delivery tube, in which the joint spacer is removably disposed for delivery compressed on an axis other than a central longitudinal axis of the joint spacer.

For some applications:
the joint spacer, when unconstrained when the bioresorbable stent is in the expanded configuration, has (a) a greatest first dimension measured along a first axis, (b) a greatest second dimension measured along a second axis perpendicular to the first axis, and (c) a greatest third dimension measured along a third axis perpendicular to the first and the second axes, and
the greatest second dimension equals at least 200% of the greatest first dimension, and the greatest third dimension equals at least 200% of the greatest first dimension. For some applications, the greatest third dimension equals at least 300% of the greatest first dimension.

For some applications, the bioresorbable stent is configured to resorb into the body of the subject between 3 and 36 months after placement in the joint. For some applications, the bioresorbable stent is configured to resorb into the body of the subject between 6 and 18 months after placement in the joint.

For some applications, the covering is bioresorbable. For some applications, the bioresorbable covering is configured to resorb into the body of the subject between 3 and 36 months after placement in the joint. For some applications, the bioresorbable covering is configured to resorb into the body of the subject between 6 and 18 months after placement in the joint.

For some applications, the bioresorbable stent and the bioresorbable covering are configured such that the bioresorbable stent resorbs into the body of the subject before the bioresorbable covering resorbs into the body of the subject.

For some applications, the covering is fluid-permeable and blood-permeable until resorbing into the body of the subject. For some applications, the covering is tissue-permeable until resorbing into the body of the subject.

For some applications, the covering includes a material selected from the group consisting of: a bioresorbable polymer, a biological tissue, and collagen.

For some applications, the covering includes the bioresorbable polymer, which includes one or more polymers selected from the group of polymers consisting of: a polylactic acid (PLA) polymer, a PLA/GA polymer, a polyglycolic acid (PGA) polymer, a polycaprolactone (PCL) polymer, a polydioxanone (PDO) polymer, and a copolymer of any of these polymers.

For some applications, the covering is non-bioresorbable. For some applications, the covering includes polyethylene terephthalate (PET).

For some applications, the covering is configured to promote tissue growth thereon, therethrough, or thereon and therethrough. For some applications, the covering is coated with a tissue-growth-promoting material. For some applications, the tissue-growth-promoting material is selected from the group consisting of: collagen, chondrocytes, and hydroxylapatite.

For some applications, the joint spacer is a subacromial spacer and the joint is a shoulder joint, and the subacromial spacer is shaped and sized so as to be insertable into a subacromial space of the shoulder joint to provide support to the shoulder joint until the bioresorbable stent resorbs into the body of the subject.

For some applications, the joint spacer is a glenohumeral spacer and the joint is a glenohumeral joint, and the glenohumeral spacer is shaped and sized so as to be insertable into the glenohumeral joint to provide support to the glenohumeral joint until the bioresorbable stent resorbs into the body of the subject.

There is further provided a method for treating a joint of a human subject, the method including: inserting a joint spacer into a space of the joint while a bioresorbable stent of the joint spacer is in a compressed configuration, a covering of the joint spacer covers an external surface of the stent; and transitioning the bioresorbable stent to an expanded configuration within the joint, such that the joint spacer provides mechanical support to the joint until the bioresorbable stent resorbs into a body of the subject.

For some applications, the covering is shaped as a pouch within which the bioresorbable stent is disposed, at least immediately upon placement within the joint. For some applications, the pouch is shaped so as to define a closed space therewithin at least immediately upon placement within the joint. For some applications, the pouch is not shaped so as to define any openings that have a cross-sectional area greater than 3 mm$^2$ at least immediately upon placement within the joint.

For some applications, the covering is fluid-permeable and blood-permeable. For some applications, the covering is tissue-permeable.

For some applications, the covering is sachet-shaped at least immediately upon placement within the joint.

For some applications, the covering is rectangular at least immediately upon placement within the joint. For some applications, the covering is square at least immediately upon placement within the joint.

For some applications, the bioresorbable stent is shaped as a partially-flattened tube when the joint spacer is unconstrained and the bioresorbable stent is in the expanded configuration.

For some applications, wherein, when the joint spacer is unconstrained and the bioresorbable stent is in the expanded configuration, the bioresorbable stent is shaped generally as a cylinder selected from the group consisting of: an elliptical cylinder and an oval cylinder. For some applications, the bioresorbable stent is shaped generally as the elliptical cylinder, and the length of the major axis of the elliptical cylinder equals at least 200% of the length of the minor axis of the elliptical cylinder when the joint spacer is unconstrained and the bioresorbable stent is in the expanded configuration. For some applications, the bioresorbable stent is shaped generally as the oval cylinder, and the distance between the axes of the oval cylinder equals at least 200% of the radii of the oval cylinder when the joint spacer is unconstrained and the bioresorbable stent is in the expanded configuration.

For some applications, inserting the joint spacer includes inserting the joint spacer while it is removably disposed in a delivery tube in a radially-compressed configuration with a central longitudinal axis of the joint spacer parallel to a longitudinal axis of the delivery tube.

For some applications, the bioresorbable stent includes a plurality of wires arranged as a braided mesh.

For some applications, the bioresorbable stent is shaped generally as an ovoid when the joint spacer is unconstrained and the bioresorbable stent is in the expanded configuration. For some applications, the bioresorbable stent is shaped generally as an ellipsoid when the joint spacer is unconstrained and the bioresorbable stent is in the expanded configuration. For some applications, the bioresorbable stent is shaped generally as a spheroid when the joint spacer is unconstrained and the bioresorbable stent is in the expanded configuration. For some applications, the bioresorbable stent is shaped generally as an oblate spheroid when the joint spacer is unconstrained and the bioresorbable stent is in the expanded configuration.

For some applications, the bioresorbable stent includes a plurality of wires arranged as a braided mesh.

For some applications, the wires cross one another within 3 mm of a first pole of the oblate spheroid and within 3 mm of a second pole of the oblate spheroid when the joint spacer is unconstrained and the bioresorbable stent is in the expanded configuration. For some applications, the length of each of the semi-axes of the oblate spheroid equals at least 300% of the length of the symmetry axis of the oblate spheroid when the joint spacer is unconstrained and the bioresorbable stent is in the expanded configuration.

For some applications, inserting the joint spacer includes inserting the joint spacer while it is removably disposed in a delivery tube in a radially-compressed configuration with a central longitudinal axis of the joint spacer parallel to a longitudinal axis of the delivery tube.

For some applications, inserting the joint spacer includes inserting the joint spacer while it is removably disposed in a delivery tube compressed on an axis other than a central longitudinal axis of the joint spacer.

For some applications, the bioresorbable stent does not include any circular cylindrical portions when the joint spacer is unconstrained and the bioresorbable stent is in the expanded configuration, at least immediately upon placement within the joint.

For some applications:

the joint spacer, when unconstrained when the bioresorbable stent is in the expanded configuration, has (a) a greatest first dimension measured along a first axis, (b) a greatest second dimension measured along a second axis perpendicular to the first axis, and (c) a greatest third dimension measured along a third axis perpendicular to the first and the second axes, and the greatest second dimension equals at least 200% of the greatest first dimension, and the greatest third dimension equals at least 200% of the greatest first dimension. For some applications, the greatest third dimension equals at least 300% of the greatest first dimension.

For some applications, the bioresorbable stent is configured to resorb into the body of the subject between 3 and 36 months after placement in the joint. For some applications, the bioresorbable stent is configured to resorb into the body of the subject between 6 and 18 months after placement in the joint.

For some applications, the covering is bioresorbable. For some applications, the bioresorbable covering is configured to resorb into the body of the subject between 3 and 36 months after placement in the joint. For some applications, the bioresorbable covering is configured to resorb into the body of the subject between 6 and 18 months after placement in the joint.

For some applications, the bioresorbable stent and the bioresorbable covering are configured such that the bioresorbable stent resorbs into the body of the subject before the bioresorbable covering resorbs into the body of the subject.

For some applications, the covering is fluid-permeable and blood-permeable until resorbing into the body of the subject. For some applications, the covering is tissue-permeable until resorbing into the body of the subject.

For some applications, the covering includes a material selected from the group consisting of: a bioresorbable polymer, a biological tissue, and collagen.

For some applications, the covering includes the bioresorbable polymer, which includes one or more polymers selected from the group of polymers consisting of: a polylactic acid (PLA) polymer, a PLA/GA polymer, a polyglycolic acid (PGA) polymer, a polycaprolactone (PCL) polymer, a polydioxanone (PDO) polymer, and a copolymer of any of these polymers.

For some applications, the covering is non-bioresorbable. For some applications, the covering includes polyethylene terephthalate (PET).

For some applications, the covering is configured to promote tissue growth thereon, therethrough, or thereon and therethrough. For some applications, the covering is coated with a tissue-growth-promoting material. For some applications, the tissue-growth-promoting material is selected from the group consisting of: collagen, chondrocytes, and hydroxylapatite.

For some applications, the bioresorbable stent includes a metal selected from the group of metals consisting of: magnesium, a magnesium alloy, calcium, a calcium alloy, iron, and an iron alloy other than steel.

For some applications, the joint spacer is a subacromial spacer, and inserting the joint spacer includes inserting the subacromial spacer into a subacromial space of a shoulder joint.

For some applications, the joint spacer is a glenohumeral spacer, and inserting the joint spacer includes inserting the glenohumeral spacer into a glenohumeral joint.

There is further provided a method for treating a joint of a human subject, the method including:
drilling a tunnel through a bone and into a space of the joint;
advancing a delivery tube through the tunnel while a joint spacer is removably disposed in the delivery tube in a compressed axially-elongated configuration;
releasing an expandable portion of the joint spacer from the delivery tube in the space of the joint;
transitioning the joint spacer to an expanded axially-shorter configuration, in which the joint spacer provides mechanical support to the joint; and
anchoring the joint spacer to the bone.

For some applications, advancing the delivery tube includes advancing the delivery tube through the tunnel while the joint spacer is removably disposed in the delivery tube in the compressed axially-elongated configuration with a central longitudinal axis thereof parallel to a central longitudinal axis of the delivery tube.

For some applications, advancing the delivery tube includes advancing the delivery tube through the tunnel while the joint spacer is removably disposed in the delivery tube in the compressed axially-elongated configuration, with the joint spacer compressed on an axis other than a central longitudinal axis of the joint spacer.

For some applications, anchoring the joint spacer to the bone includes anchoring the joint spacer to a wall of the tunnel.

For some applications, anchoring the joint spacer to the bone includes anchoring the joint spacer to a surface of the bone facing the space of the joint.

For some applications, drilling the tunnel includes drilling the tunnel through a humerus.

For some applications, the joint spacer is a subacromial spacer, and releasing the expandable portion of the joint spacer includes releasing the expandable portion of the joint spacer from the delivery tube in a subacromial space of the joint.

For some applications, the joint spacer is a glenohumeral spacer, and releasing the expandable portion of the joint spacer includes releasing the expandable portion of the joint spacer from the delivery tube in a space of a glenohumeral joint.

For some applications, drilling the tunnel includes drilling the tunnel through an acromion.

For some applications, the joint spacer is a subacromial spacer, and releasing the expandable portion of the joint spacer includes releasing the expandable portion of the joint spacer from the delivery tube in a subacromial space of the joint.

For some applications, transitioning includes transitioning the joint spacer to the expanded axially-shorter configuration while releasing the expandable portion of the joint spacer from the delivery tube in the space of the joint.

For some applications, transitioning includes transitioning the joint spacer to the expanded axially-shorter configuration after releasing the expandable portion of the joint spacer from the delivery tube in the space of the joint.

For some applications:
the joint spacer includes a stent and a covering that covers an external surface of the stent, and
releasing includes releasing the expandable portion of the joint spacer from the delivery tube in the space of the joint such that the stent of the joint spacer generally assumes an ovoid shape.

For some applications, the stent includes a plurality of wires arranged as a braided mesh.

For some applications, releasing includes releasing the expandable portion of the joint spacer from the delivery tube in the space of the joint such that the stent of the joint spacer generally assumes an oblate-spheroidal shape.

For some applications, releasing includes releasing the expandable portion of the joint spacer from the delivery tube in the space of the joint such that the wires cross one another within 3 mm a first pole of the oblate-spheroidal shape and within 3 mm of a second pole of the oblate-spheroidal shape.

For some applications, releasing includes releasing the expandable portion of the joint spacer from the delivery tube in the space of the joint such that each of the semi-axes of the oblate-spheroid shape equals at least 300% of the symmetry axis of the oblate-spheroid shape.

For some applications, the stent is bioresorbable. For some applications, the covering is bioresorbable. Alternatively, the covering is non-bioresorbable.

The present disclosure will be more fully understood from the following detailed description of embodiments thereof, taken together with the drawings.

BRIEF DESCRIPTION OF THE DRAWINGS

FIGS. 1A-D are schematic illustrations of a joint spacer for treatment of a joint of a human subject, in a compressed configuration;

FIGS. 2A-C are schematic illustrations of the joint spacer of FIGS. 1A-D in an expanded configuration;

DETAILED DESCRIPTION

Figure 3A:
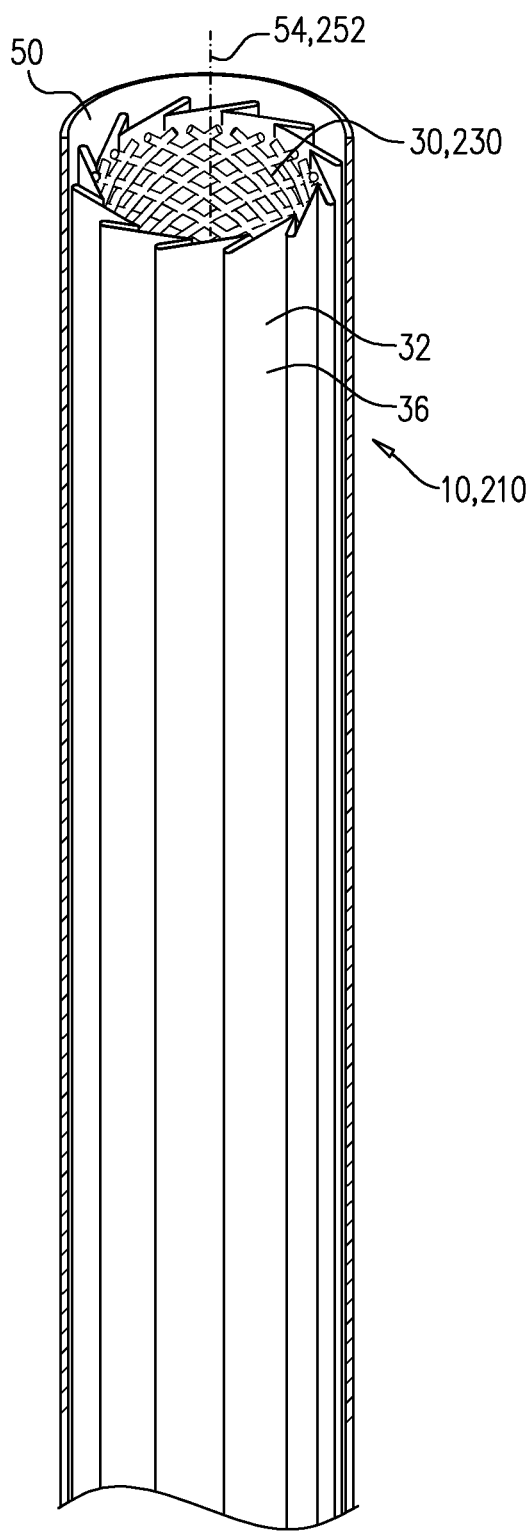
FIGS. 3A-C are schematic illustrations of another joint spacer for treatment of a joint of a human subject, in a compressed configuration.
Figure 3B:
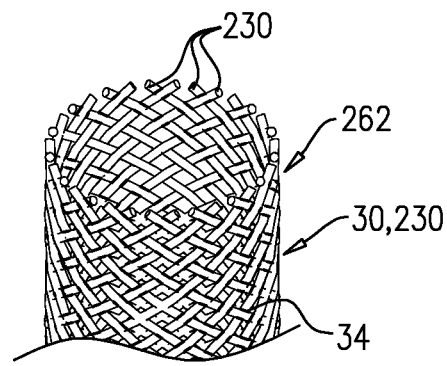
Figure 3C:
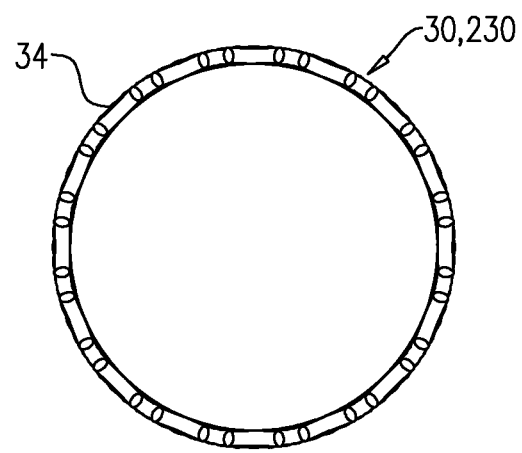

Embodiments of the present disclosure provide a joint spacer 10 for treatment of a joint of a human subject.

Reference is made to FIGS. 1A-D and 2A-C, which are schematic illustrations of a joint spacer 110 for treatment of a joint of a human subject, in compressed and expanded configurations, respectively. Reference is also made to FIGS. 3A-C and 4A-D, which are schematic illustrations of a joint spacer 210 for treatment of a joint of a human subject, in compressed and expanded configurations, respectively. Joint spacers 110 and 210 are respective configurations of joint spacer 10.

Joint spacer 10 includes:
a bioresorbable stent 30 having a compressed configuration, such as shown in FIGS. 1A-D and 3A-C, and an expanded configuration, such as shown in FIGS. 2A-C and 4A-D; and
a covering 32 that covers an external surface 34 of stent 30 (i.e., an external structure of the structure defined by stent 30, rather than only the external surfaces of individual struts of the stent).

Joint spacer 10 is configured to be inserted into a space of the joint, and is shaped, when bioresorbable stent 30 is in the expanded configuration, to provide mechanical support to the joint until bioresorbable stent 30 resorbs into a body of the subject while new tissue is remodeled. For some applications, joint spacer 10 may simulate at the size or shape of a natural bursa.

For some applications, joint spacer 10 is a subacromial spacer and the joint is a shoulder joint, and the subacromial spacer is shaped and sized so as to be insertable into a subacromial space of the shoulder joint to provide support to the shoulder joint until bioresorbable stent 30 resorbs into the body of the subject. For example, the subacromial spacer may be used for treating a rotator cuff injury. For other applications, joint spacer 10 is a glenohumeral spacer and the joint is a glenohumeral joint, and the glenohumeral spacer is shaped and sized so as to be insertable into the glenohumeral joint to provide support to the glenohumeral joint until bioresorbable stent 30 resorbs into the body of the subject for treating glenohumeral arthritis. Alternatively, joint spacer 10 is shaped and sized to be inserted into another joint, such as knee, hip, ankle, or hand (e.g., CMC1) joint.

Typically, bioresorbable stent 30 is configured to resorb into the body of the subject between 3 and 36 months after placement in the joint, such as between 6 and 18 months after placement in the joint, e.g., about one year after placement in the joint. This period of time may allow soft tissue to grow into the space defined and structurally supported by joint spacer 10 while bioresorbable stent 30 resorbs into the body, thereby providing long-term treatment to the joint without the long-term presence of a prosthetic implant.

For some applications, bioresorbable stent 30 includes a metal selected from the group of metals consisting of: magnesium, a magnesium alloy, calcium, a calcium alloy, iron, and an iron alloy other than steel.

For some applications, covering 32 is shaped as a pouch 36 within which bioresorbable stent 30 is disposed, at least immediately upon placement within the joint. (For applications in which covering 32 is bioresorbable, such as described herein, covering 32 ceases to be shaped as pouch 36 at some point during the bioresorption of covering 32; the same is true of many of the other features described herein.) For some applications, pouch 36 is shaped so as to define a closed space therewithin at least immediately upon placement within the joint. For some applications, pouch 36 is not shaped so as to define any openings that have a cross-sectional area greater than 3 mm$^2$ at least immediately upon placement within the joint.

Typically, covering 32 is fluid-permeable and blood-permeable. For applications in which covering 32 is bioresorbable, such as described herein, covering 32 is typically fluid-permeable and blood-permeable until resorbing into the body of the subject. Typically, covering 32 is tissue-permeable. For applications in which covering 32 is bioresorbable, such as described herein, covering 32 is typically tissue-permeable until resorbing into the body of the subject.

For some applications, covering 32 is bioresorbable. For some applications, bioresorbable covering 32 is configured to resorb into the body of the subject between 3 and 36 months after placement in the joint, such as between 6 and 18 months after placement in the joint, e.g., about one year after placement in the joint. For some applications, covering 32 includes a material selected from the group consisting of: a bioresorbable polymer, a biological tissue (e.g., bovine or equine fascia lata), and collagen. For some applications in which the material is the bioresorbable polymer, the bioresorbable polymer includes one or more polymers selected from the group of polymers consisting of: a polylactic acid (PLA) polymer, a PLA/GA polymer, a polyglycolic acid (PGA) polymer, a polycaprolactone (PCL) polymer, a polydioxanone (PDO) polymer, and a copolymer of any of these polymers.

For some applications, bioresorbable stent 30 and bioresorbable covering 32 are configured such that bioresorbable stent 30 resorbs into the body of the subject before bioresorbable covering 32 resorbs into the body of the subject. As a result, bioresorbable covering may protect the joint from direct exposure to bioresorbable stent 30 until bioresorbable stent 30 resorbs.

For other applications, covering 32 is non-bioresorbable. For some of these applications, covering 32 includes polyethylene terephthalate (PET).

For some applications, covering 32 is configured to promote tissue growth thereon and/or therethrough, into the space defined by the spacer. For example, covering 32 may be coated with a tissue-growth-promoting material, e.g., selected from the group consisting of: collagen, chondrocytes, and hydroxylapatite.

Typically, unlike endovascular stent-grafts, joint spacer 10 is not shaped so as to allow directional blood flow therethrough, at least immediately upon placement within the joint. Typically, unlike endovascular stent-grafts, covering 32 does not define a tubular lumen therethrough when joint spacer 10 is unconstrained and bioresorbable stent 30 is in the expanded configuration, at least immediately upon placement within the joint. Typically, unlike endovascular stent-grafts, bioresorbable stent 30 does not include any circular cylindrical portions when joint spacer 10 is unconstrained and bioresorbable stent 30 is in the expanded configuration, at least immediately upon placement within the joint.

Reference is made to FIGS. 1A-D and 2A-C. For some applications, bioresorbable stent 30 of joint spacer 110 includes a bioresorbable stent 130. For some applications, bioresorbable stent 130 is manufactured by laser cutting. For some applications, bioresorbable stent 130 is shaped as a partially-flattened tube 140 when joint spacer 110 is unconstrained and bioresorbable stent 30 is in the expanded configuration. For some applications, when joint spacer 110 is unconstrained and bioresorbable stent 130 is in the expanded configuration, bioresorbable stent 30 is shaped generally as a cylinder 142.

For some applications, bioresorbable stent 130 is shaped generally as an elliptical cylinder. For example, the length L1 of the major axis of the elliptical cylinder may equal at least 200% of the length L2 of the minor axis of the elliptical cylinder when joint spacer 110 is unconstrained and bioresorbable stent 130 is in the expanded configuration. For some applications, bioresorbable stent 130 is shaped generally as an oval or elliptic cylinder, and the distance between the axes of the oval cylinder equals at least 200% of the radii of the oval cylinder when joint spacer 110 is unconstrained and bioresorbable stent 130 is in the expanded configuration.

Reference is still made to FIGS. 1A-D and 2A-C. For some applications, covering 32 is sachet-shaped at least immediately upon placement within the joint. Alternatively or additionally, for some applications, covering 32 is rectangular (e.g., square), elliptical, oval, or circular at least immediately upon placement within the joint.

Reference is made to FIG. 2A. For some applications, joint spacer 110, when unconstrained when bioresorbable stent 130 is in the expanded configuration, has (a) a greatest first dimension D1 measured along a first axis 144A, (b) a greatest second dimension D2 measured along a second axis 144B perpendicular to first axis 144A, and (c) a greatest third dimension D3 measured along a third axis 144C perpendicular to first axis 144A and second axis 144B. Typically, the greatest second dimension D2 equals at least 200% of the greatest first dimension D1, and the greatest third dimension D3 equals at least 200% of the greatest first dimension D1, such as at least 300% of the greatest first dimension D1.

For some applications, such as shown in FIG. 1A, a delivery tube 50 is provided, in which joint spacer 110 is removably disposed for delivery in a radially-compressed configuration with a central longitudinal axis 152 thereof parallel to a longitudinal axis 54 of delivery tube 50. Delivery tube 50 may enable arthroscopic insertion of joint spacer 110 into the joint. As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Reference is made to FIGS. 3A-C and 4A-D. For some applications, bioresorbable stent 30 of joint spacer 210 includes a bioresorbable stent 230, which includes a plurality of wires 260 arranged as a braided mesh 262.

For some applications, bioresorbable stent 230 is shaped generally as an ovoid when joint spacer 210 is unconstrained and bioresorbable stent 230 is in the expanded configuration.

For some applications, bioresorbable stent 230 is shaped generally as an ellipsoid when joint spacer 210 is unconstrained and bioresorbable stent 230 is in the expanded configuration. For some applications, bioresorbable stent 230 is shaped generally as a spheroid when joint spacer 210 is unconstrained and bioresorbable stent 230 is in the expanded configuration. For some applications, bioresorbable stent 230 is shaped generally as an oblate spheroid 270 when joint spacer 210 is unconstrained and bioresorbable stent 230 is in the expanded configuration. For some applications, wires 260 cross one another within 3 mm of a first pole 272A of oblate spheroid 270 and within 3 mm of a second pole 272B of oblate spheroid 270 when joint spacer 210 is unconstrained and bioresorbable stent 230 is in the expanded configuration. For some applications, the length of each of the semi-axes of oblate spheroid 270 equals at least 200% of the length of the symmetry axis of the oblate spheroid when joint spacer 210 is unconstrained and bioresorbable stent 230 is in the expanded configuration.

Figure 4B:
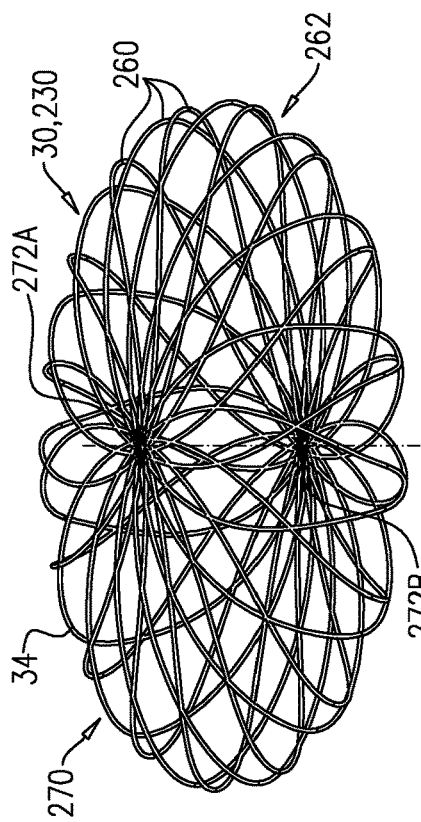
FIGS. 4A-D are schematic illustrations of the joint spacer of FIGS. 3A-C in an expanded configuration.
Figure 4D:
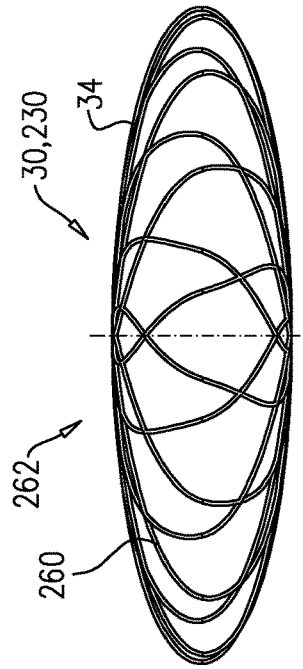
Figure 4A:
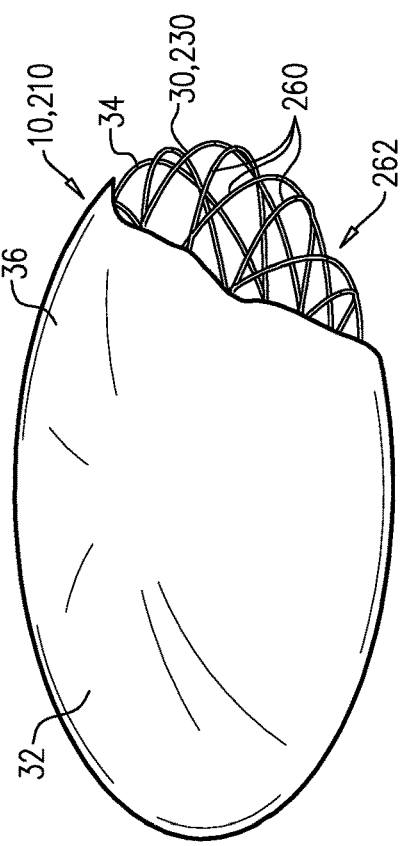
Figure 4C:
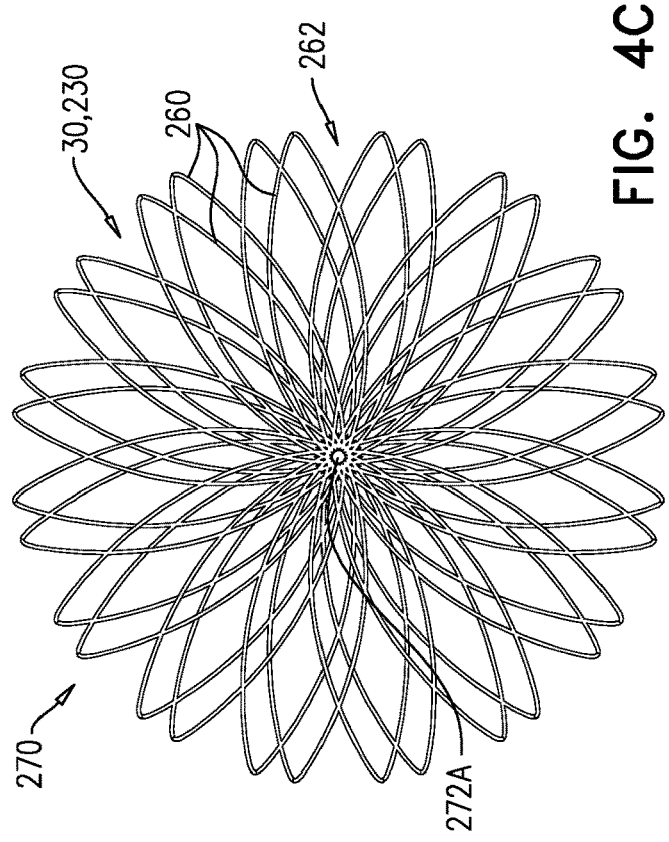

Reference is made to FIG. 4A. For some applications, joint spacer 210, when unconstrained when bioresorbable stent 230 is in the expanded configuration, has (a) a greatest first dimension measured along a first axis, (b) a greatest second dimension measured along a second axis perpendicular to the first axis, and (c) a greatest third dimension measured along a third axis perpendicular to the first axis and the second axis (not labeled in FIG. 4A, but similar to the dimensions labeled in FIG. 2A, mutatis mutandis). Typically, the greatest second dimension equals at least 200% of the greatest first dimension, and the greatest third dimension equals at least 200% of the greatest first dimension, such as at least 300% of the greatest first dimension.

For some applications, such as shown in FIG. 3A, delivery tube 50 is provided, in which joint spacer 210 is removably disposed for delivery in a compressed axially-elongated configuration with a central longitudinal axis 252 thereof parallel to central longitudinal axis 54 of delivery tube 50. For other applications, joint spacer 210 is removably disposed in delivery tube 50 for delivery compressed on an axis other than central longitudinal axis 252 of joint spacer 210, i.e., is collapsed asymmetrically. Delivery tube 50 may enable arthroscopic insertion of joint spacer 210 into the joint.

Figure 5A:
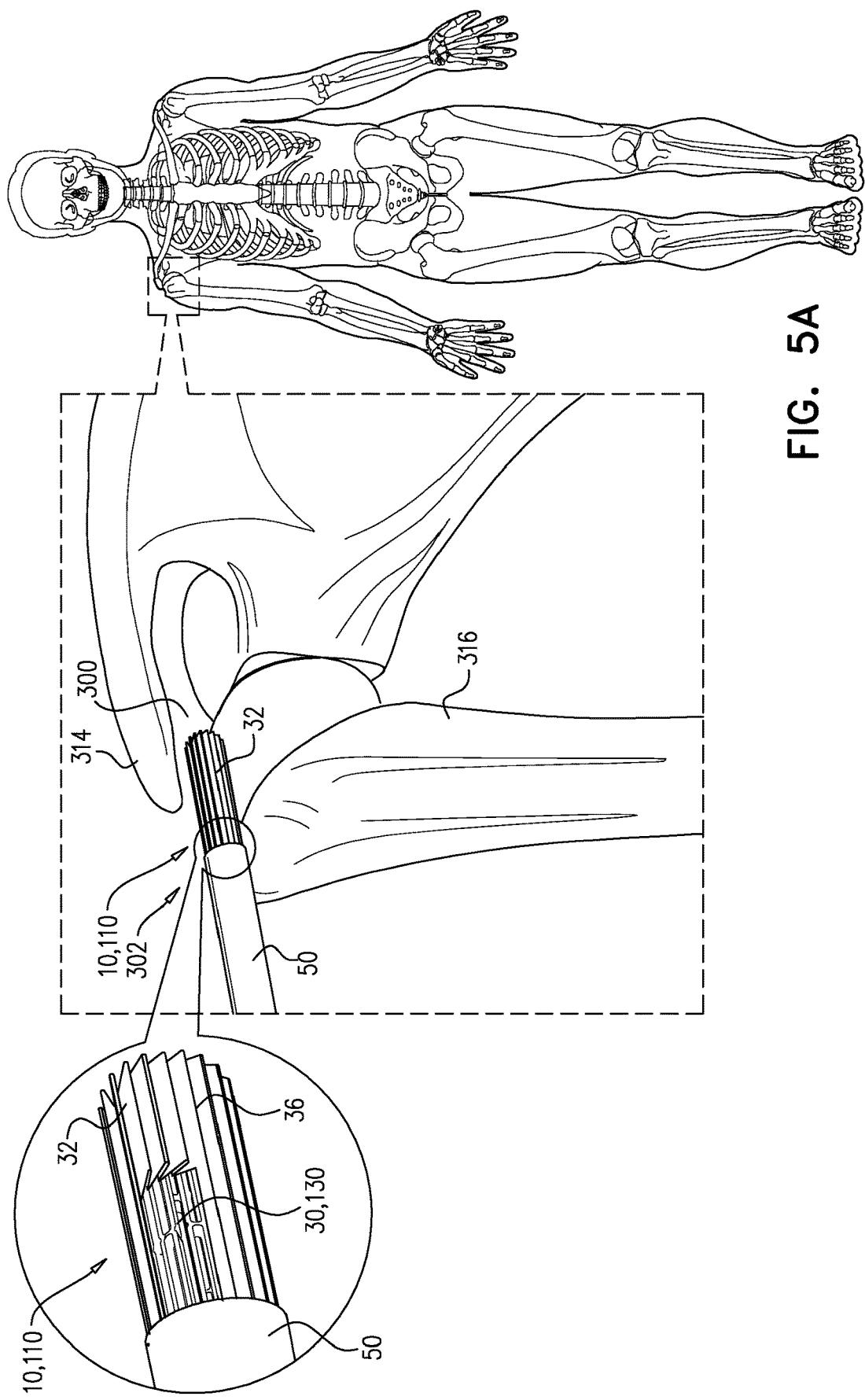
FIGS. 5A-B are schematic illustrations of a method of deploying the joint spacer of FIGS. 1A-D and 2A-C into a subacromial space of a shoulder joint.
Figure 5B:
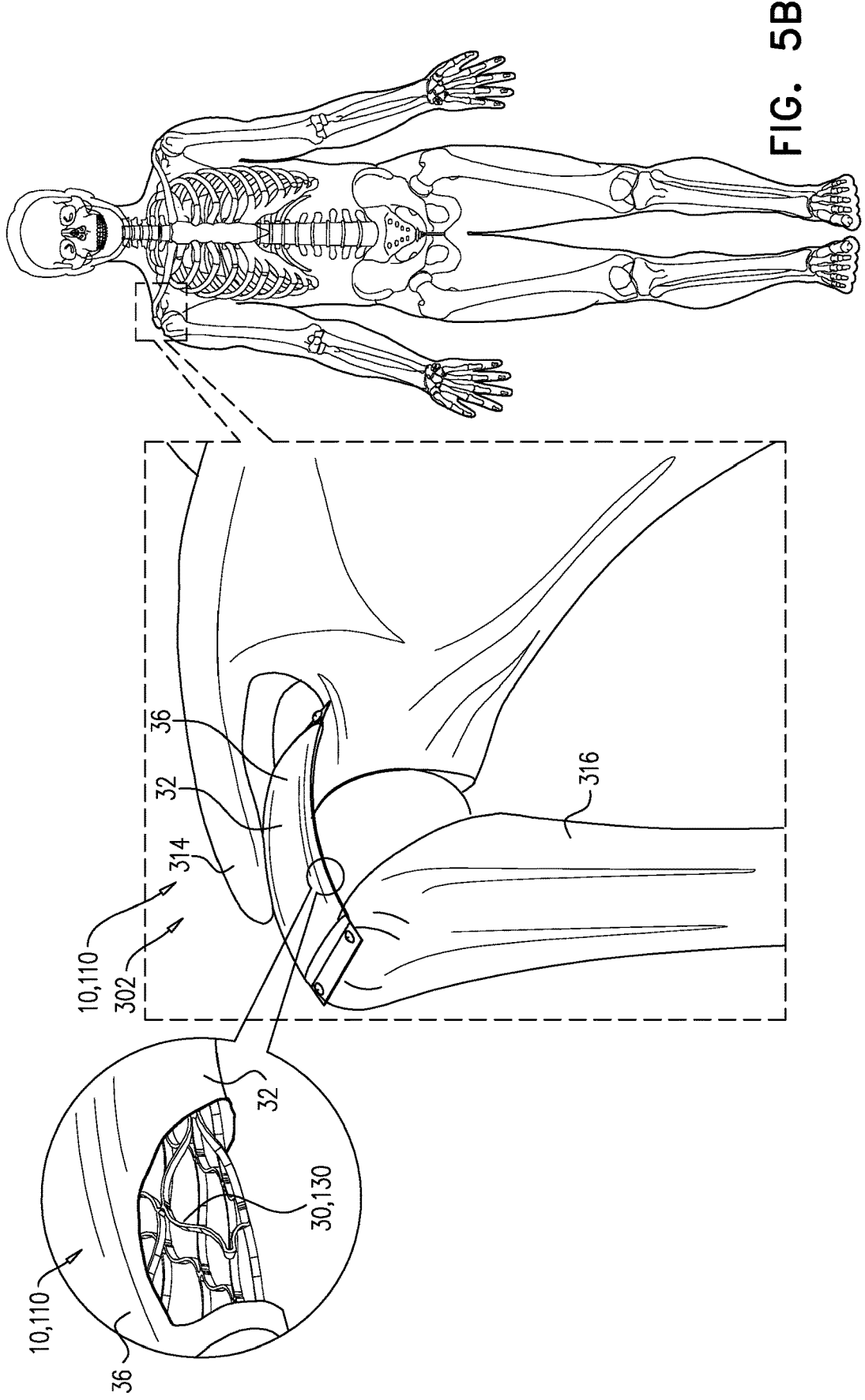

Reference is now made to FIGS. 5A-B, which are schematic illustrations of a method of deploying joint spacer 110 into a subacromial space 300 of a shoulder joint 302. In the illustrated method, joint spacer 110 is a subacromial spacer 110; alternatively, joint spacer 110 is introduced into another joint and/or space, using this method mutatis mutandis.

As shown in FIG. 5A, subacromial spacer 110 is arthroscopically inserted into subacromial space 300 while bioresorbable stent 130 of joint spacer 110 is in the compressed configuration. Typically, this insertion is performed with subacromial spacer 110 removably disposed in delivery tube 50 in a radially-compressed configuration, such as with central longitudinal axis 152 of subacromial spacer 110 parallel to longitudinal axis 54 of delivery tube 50.

As shown in FIG. 5B, bioresorbable stent 130 is transitioned to the expanded configuration within the joint, such that joint spacer 110 provides mechanical support to the joint until bioresorbable stent 130 resorbs into a body of the subject. For example, bioresorbable stent 130 may be balloon-expanded, as is known in the stent art.

Figure 6A:
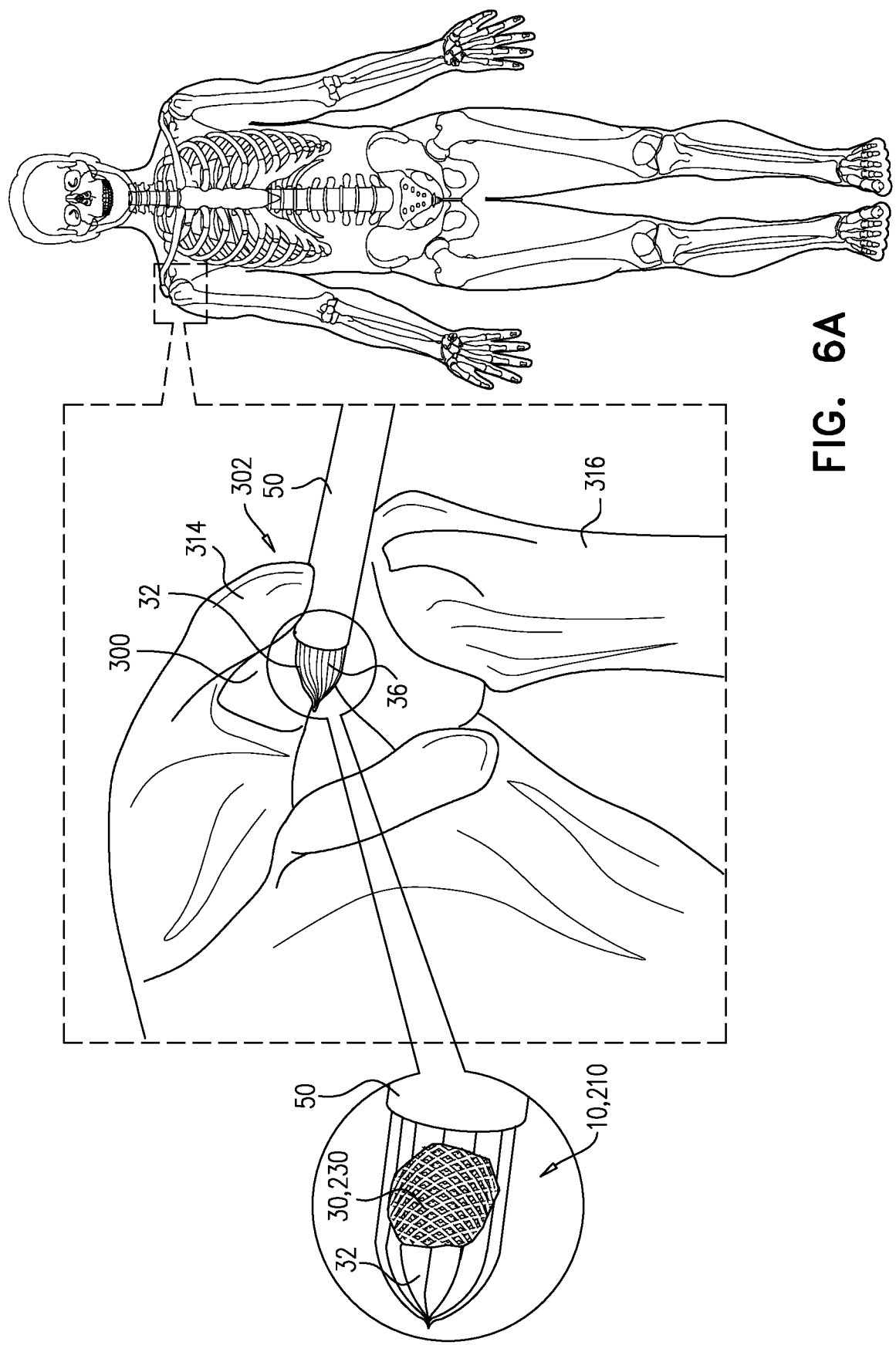
FIGS. 6A-B are schematic illustrations of a method of deploying the joint spacer of FIGS. 3A-C and 4A-D into a subacromial space of a shoulder joint.
Figure 6B:
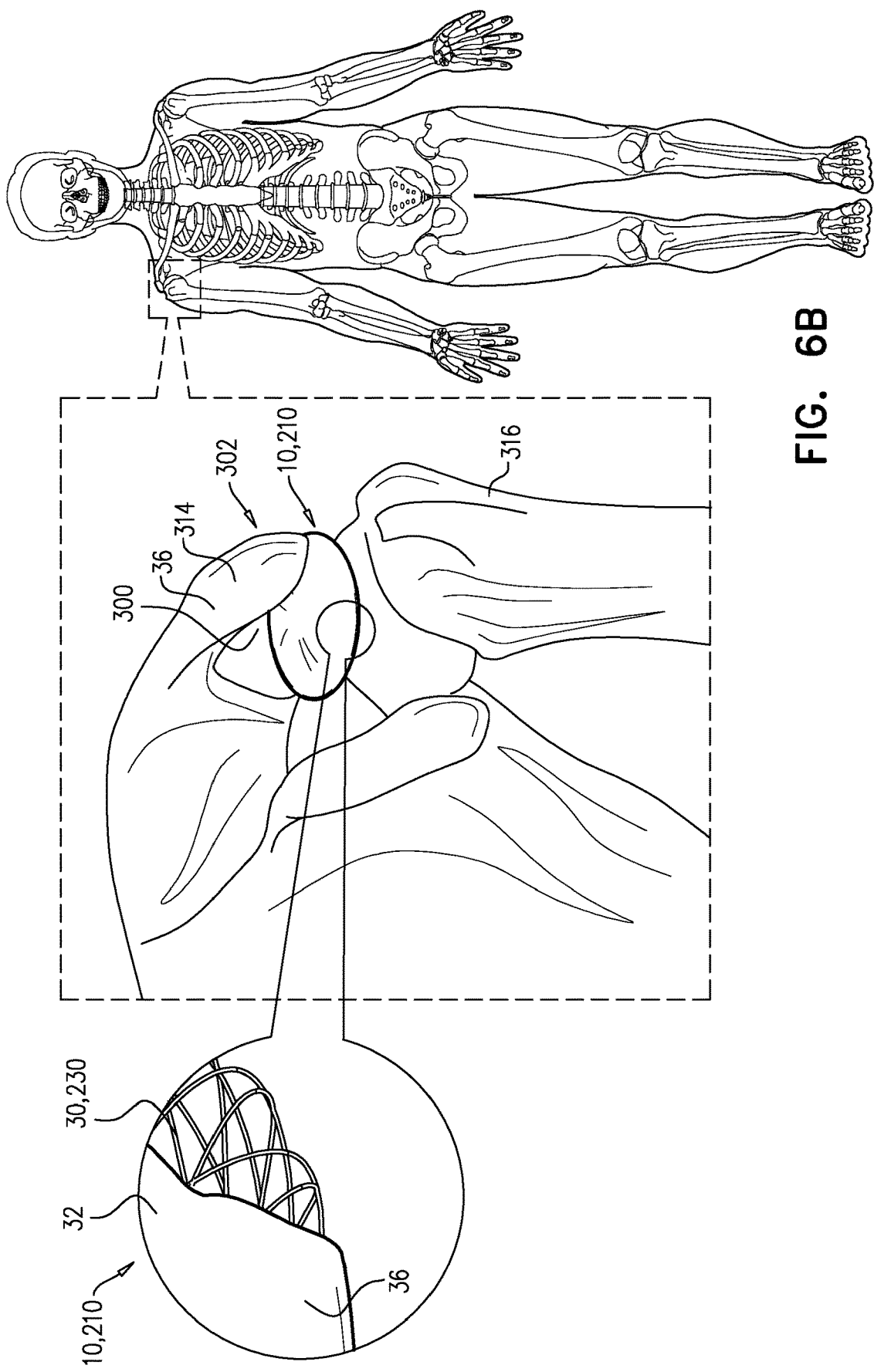

Reference is now made to FIGS. 6A-B, which are schematic illustrations of a method of deploying joint spacer 210 into subacromial space 300 of shoulder joint 302. In the illustrated method, joint spacer 210 is a subacromial spacer 210; alternatively, joint spacer 210 is introduced into another joint and/or space, using this method mutatis mutandis.

As shown in FIG. 6A, subacromial spacer 210 is arthroscopically inserted into subacromial space 300 while bioresorbable stent 230 of joint spacer 210 is in the compressed configuration. Typically, this insertion is performed with subacromial spacer 210 removably disposed in delivery tube 50 in a radially-compressed configuration, such as with central longitudinal axis 252 of subacromial spacer 210 parallel to longitudinal axis of delivery tube 50, as shown in FIGS. 1A-D, or compressed on an axis other than central longitudinal axis 252 of subacromial spacer 210.

As shown in FIG. 6B, bioresorbable stent 230 is transitioned to the expanded configuration within the joint, such that joint spacer 210 provides mechanical support to the joint until bioresorbable stent 230 resorbs into a body of the subject. For example, bioresorbable stent 230 may be expanded by axially shortening the stent, or bioresorbable stent 230 may be balloon-expanded, as is known in the stent art.

Figure 7B:
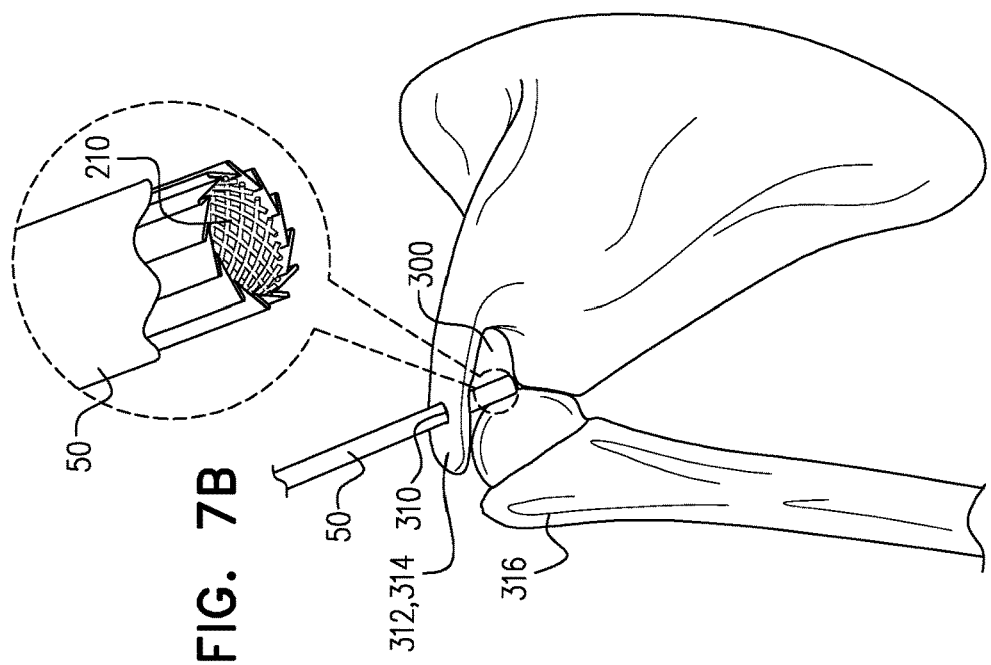
FIGS. 7A-C are schematic illustrations of another method of deploying the joint spacer of FIGS. 3A-C and 4A-D into a subacromial space of a shoulder joint.
Figure 7A:
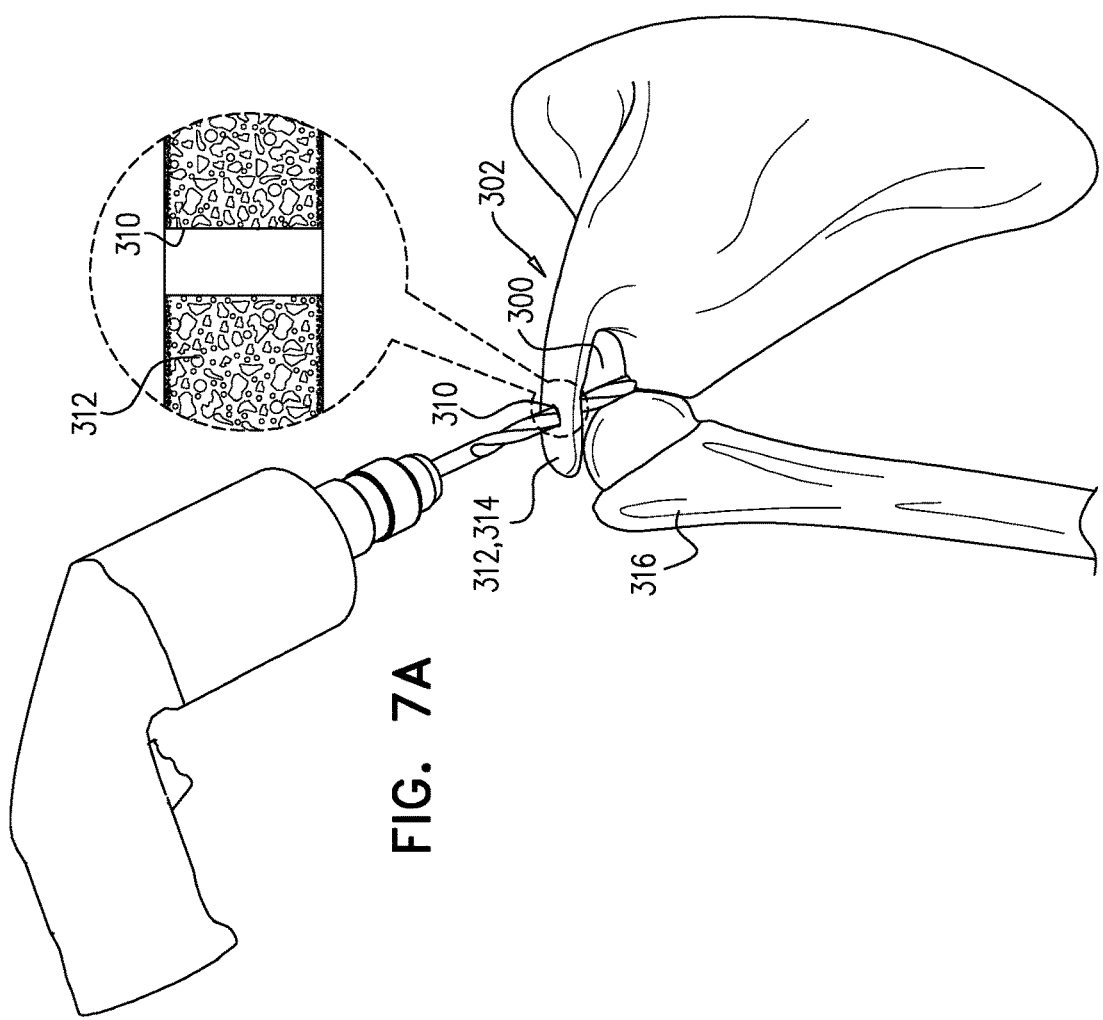
Figure 7C:
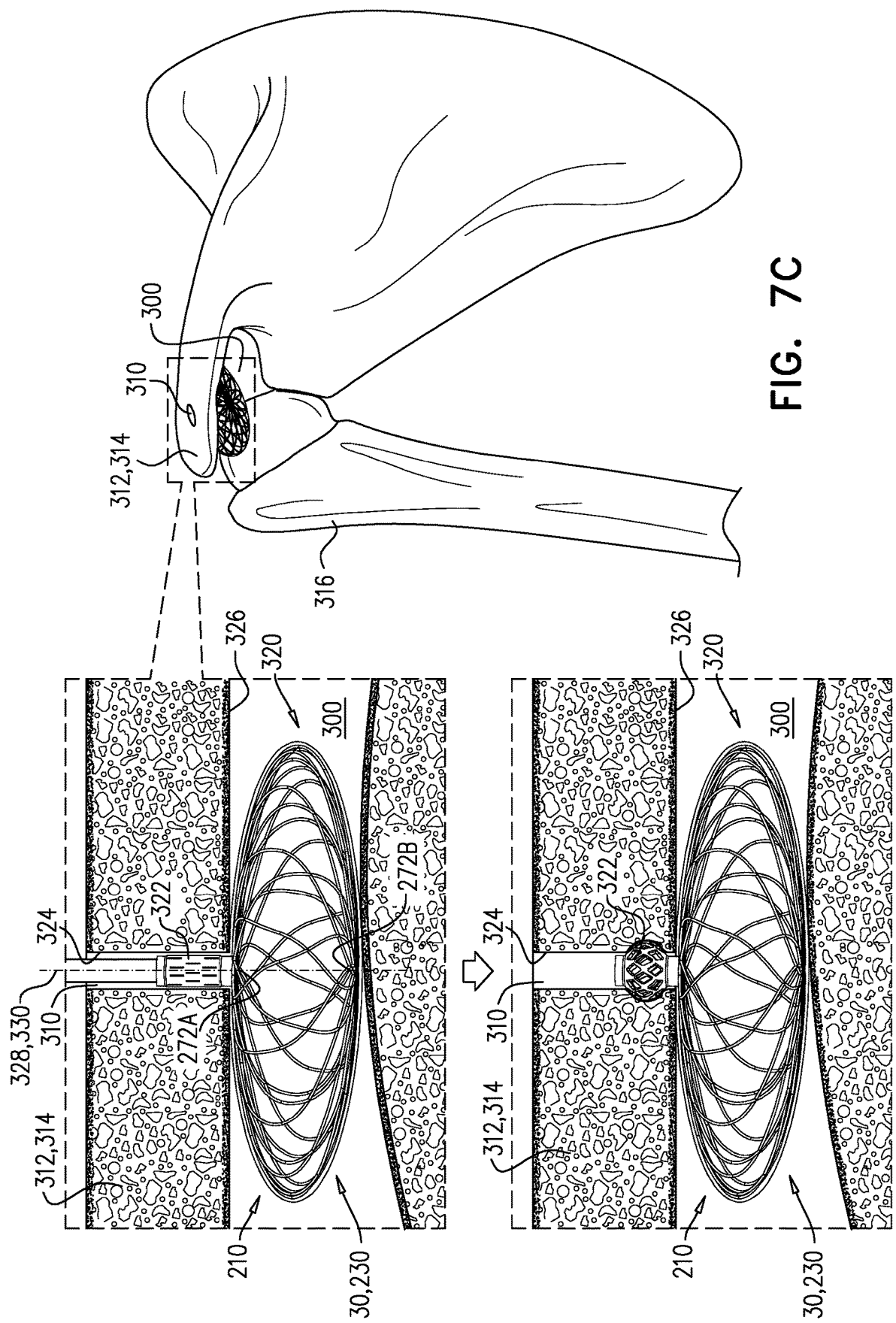

Reference is now made to FIGS. 7A-C, which are schematic illustrations of another method of deploying joint spacer 210 into subacromial space 300 of shoulder joint 302. In the illustrated method, joint spacer 210 is a subacromial spacer 210; alternatively, joint spacer 210 is introduced into another joint and/or space, such as a space of a glenohumeral joint 304, using this method mutatis mutandis, such as described herein with reference to FIGS. 8A-C. The method may also be used for other joint spacers.

As shown in FIG. 7A, a tunnel 310 is drilled through a bone 312 and into subacromial space 300 of shoulder joint 302. For some applications, bone 312 is an acromion 314, such as shown.

As shown in FIG. 7B, delivery tube 50 is advanced through tunnel 310 while subacromial spacer 210 is removably disposed in delivery tube 50 in a compressed axially-elongated configuration, either (a) with central longitudinal axis 252 thereof parallel to central longitudinal axis 54 of delivery tube 50, or (b) compressed on an axis other than central longitudinal axis 252 of subacromial spacer 210.

As shown in FIG. 7C, an expandable portion 320 of subacromial spacer 210 is released from delivery tube 50 in subacromial space 300 of shoulder joint 302, and subacromial spacer 210 is transitioned to an expanded axially-shorter configuration, in which subacromial spacer 210 provides mechanical support to shoulder joint 302. Subacromial spacer 210 is transitioned to the expanded axially-shorter configuration while expandable portion 320 of subacromial spacer 210 is being released from delivery tube 50 in subacromial space 300, or after expandable portion 320 of subacromial spacer 210 has been released from delivery tube 50 in subacromial space 300.

Also as shown in FIG. 7C, subacromial spacer 210 is anchored to bone 312, such as using an expandable anchor 322 that subacromial spacer 210 includes in this configuration. For some applications, such as shown in FIG. 7C, subacromial spacer 210 is anchored to a wall 324 of tunnel 310. For other applications, subacromial spacer 210 is anchored to a surface 326 of bone 312 facing space 300 of the joint, e.g., with clips (configuration not shown). The anchoring may be performed before or after subacromial spacer 210 is transitioned to the expanded axially-shorter configuration. Optionally, anchor 322 is disposed at one of first and second poles 272A and 272B. Optionally, a central longitudinal axis 328 of anchor 322 is coaxial with an axis 330 of bioresorbable stent 230 defined by first and second poles 272A and 272B.

Figure 8B:
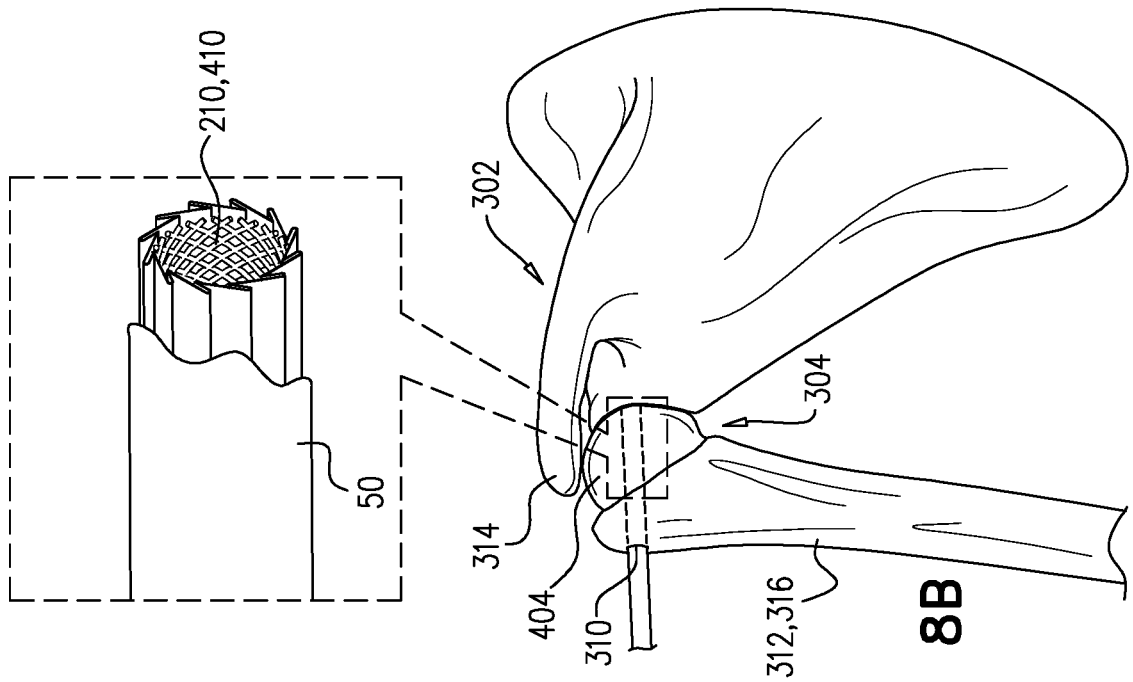
FIGS. 8A-C are schematic illustrations of a method of deploying the joint spacer of FIGS. 3A-C and 4A-D into a space of a glenohumeral joint.
Figure 8A:
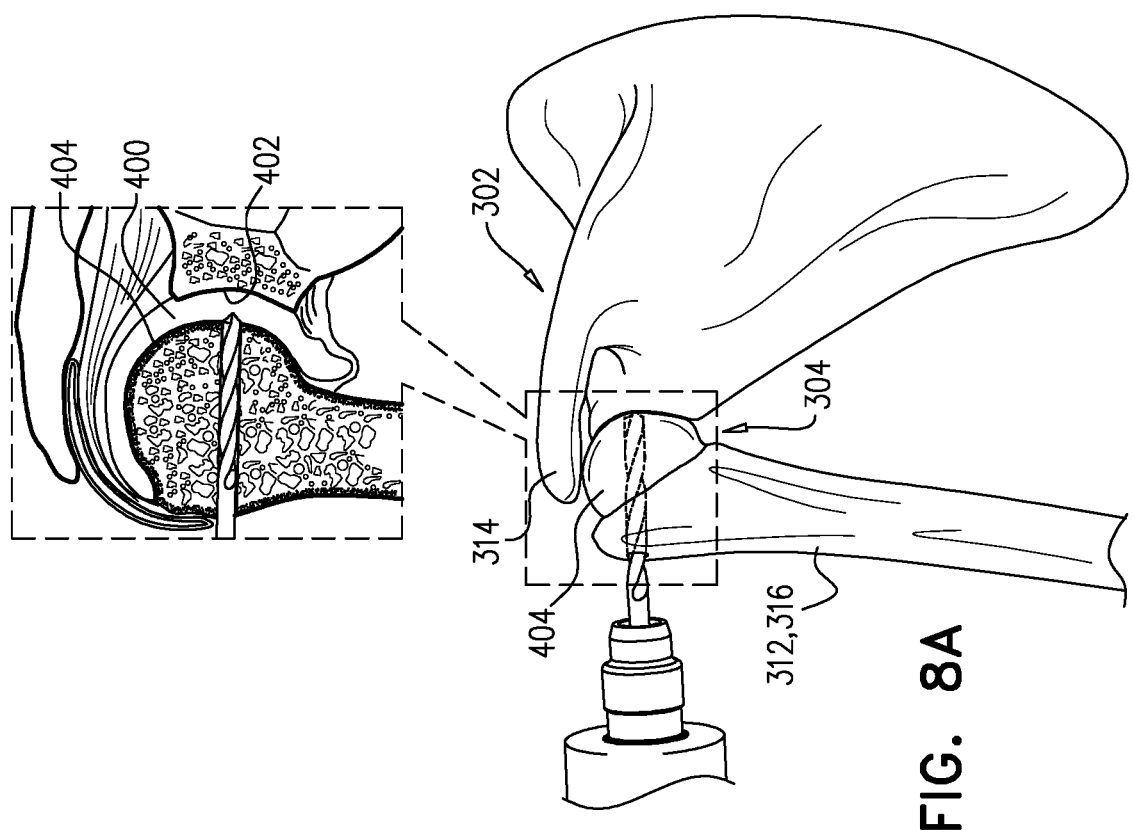
Figure 8C:
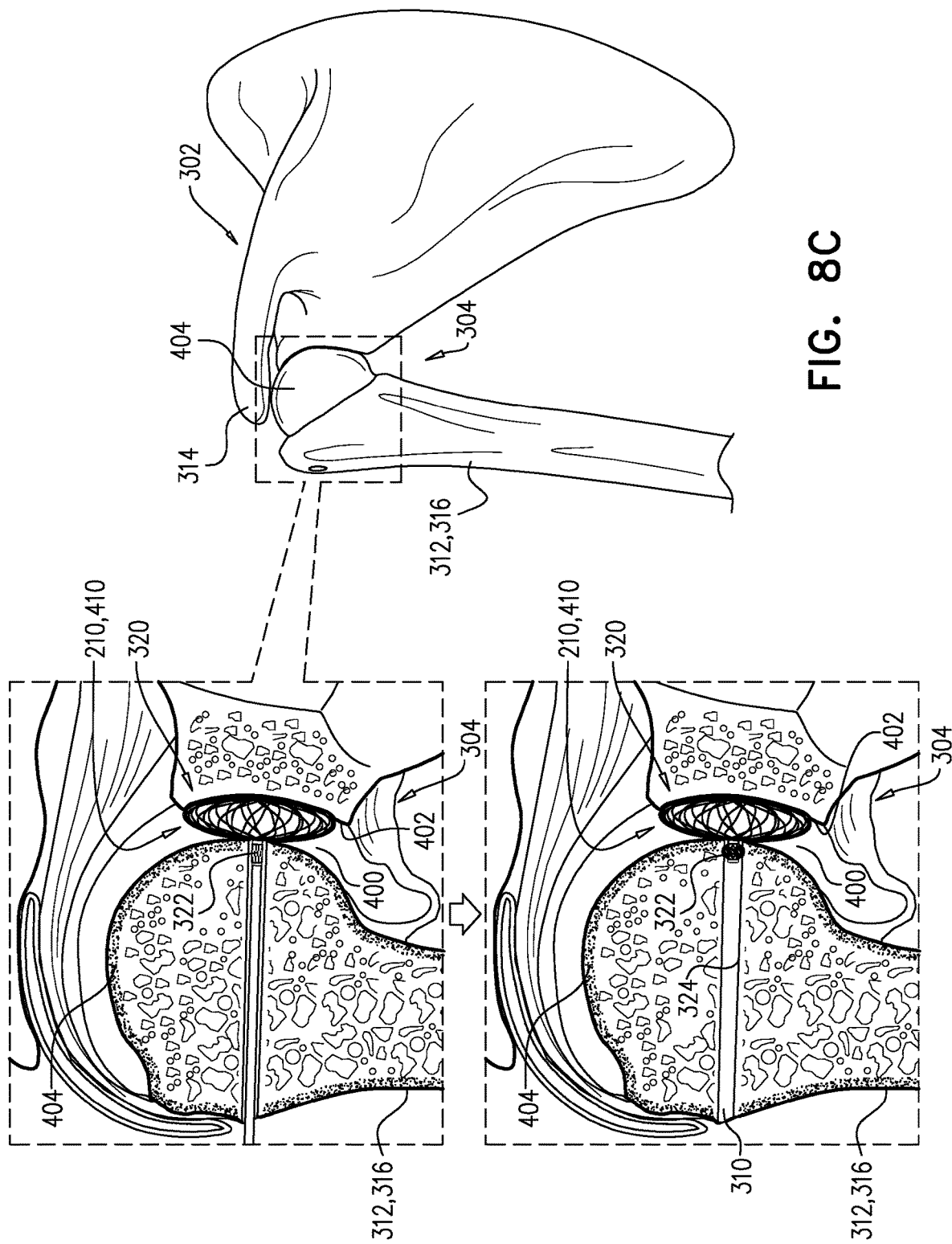

Reference is now made to FIGS. 8A-C, which are schematic illustrations of a method of deploying joint spacer 210 into a space 400 of glenohumeral joint 304 (between the glenoid cavity 402 and the humeral head 404). In the illustrated method, joint spacer 210 is a glenohumeral spacer 410.

As shown in FIG. 8A, a tunnel 310 is drilled through humerus 316 and into space 400 of glenohumeral joint 304.

As shown in FIG. 8B, delivery tube 50 is advanced through tunnel 310 while glenohumeral spacer 410 is removably disposed in delivery tube 50 in a compressed axially-elongated configuration, either (a) with central longitudinal axis 252 thereof (labeled in FIG. 3A) parallel to central longitudinal axis 54 of delivery tube 50, or (b) compressed on an axis other than central longitudinal axis 252 of glenohumeral spacer 410.

As shown in FIG. 8C, expandable portion 320 of glenohumeral spacer 410 is released from delivery tube 50 in space 400 of glenohumeral joint 304, and glenohumeral spacer 410 is transitioned to an expanded axially-shorter configuration, in which glenohumeral spacer 410 provides mechanical support to glenohumeral joint 304. Glenohumeral spacer 410 is transitioned to the expanded axially-shorter configuration while expandable portion 320 of glenohumeral spacer 410 is being released from delivery tube 50 in space 400 of glenohumeral joint 304, or after expandable portion 320 of glenohumeral spacer 410 has been released from delivery tube 50 in space 400 of glenohumeral joint 304.

Also as shown in FIG. 8C, glenohumeral spacer 410 is anchored to humerus 316, such as using expandable anchor 322 that glenohumeral spacer 410 includes in this configuration. For some applications, such as shown in FIG. 8C, glenohumeral spacer 410 is anchored to wall 324 of tunnel 310. Alternatively, glenohumeral spacer 410 may be anchored (a) at the outer surface of humerus 316, outside of tunnel 310 at its lateral opening, or (b) to the glenoid side. The anchoring may be performed before or after glenohumeral spacer 410 is transitioned to the expanded axially-shorter configuration.

Figure 9A:
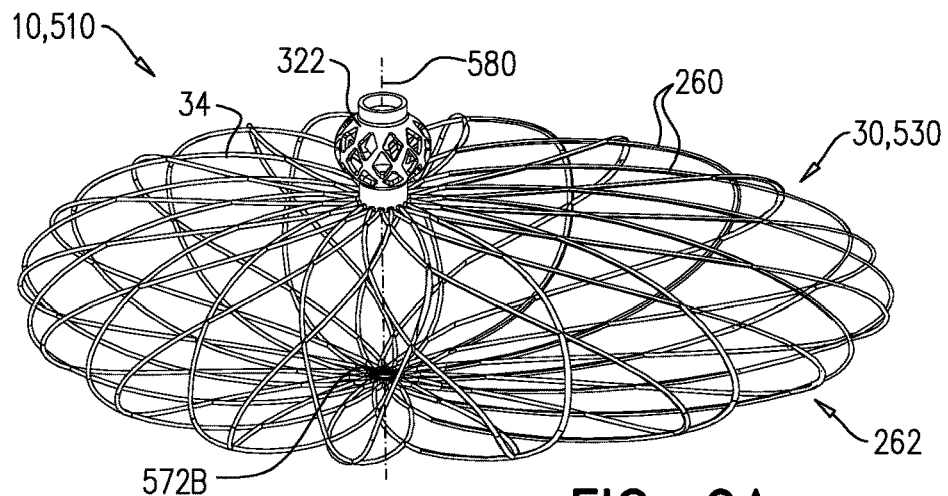
FIGS. 9A-C are schematic illustrations of another joint spacer in an expanded configuration.
Figure 9B:
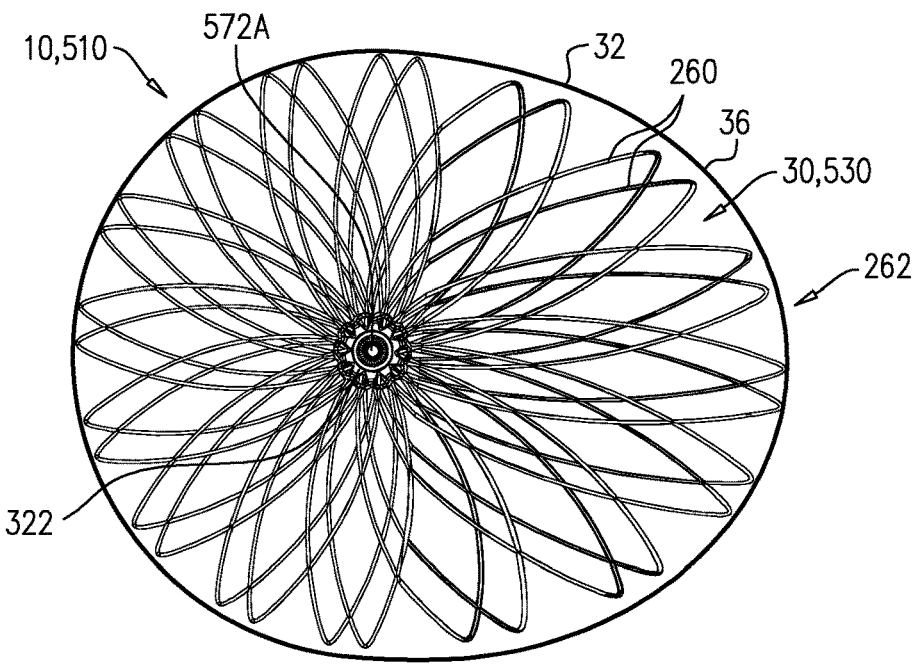
Figure 9C:
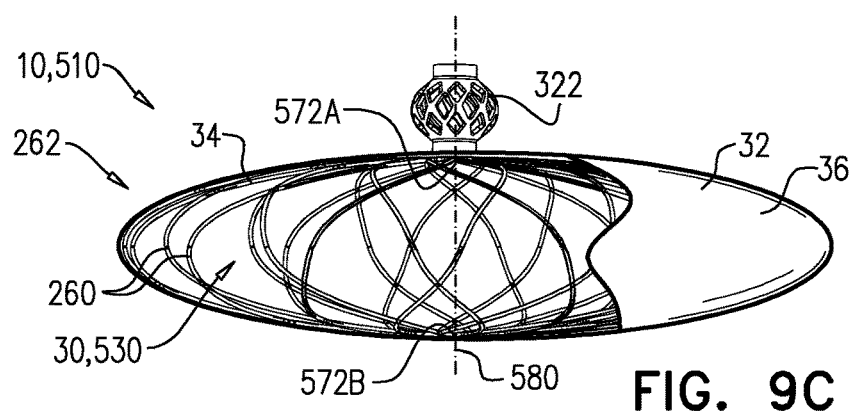

Reference is now made to FIGS. 9A-C, which are schematic illustrations of another joint spacer 510 in an expanded configuration. Except as described below, joint spacer 510 is similar to joint spacer 210, described with reference to FIGS. 3A-C and 4A-D, and may implement any of the features thereof, mutatis mutandis. Joint spacer 510 is a configuration of joint spacer 10. (Covering 32 is not shown in FIG. 9A.)

A bioresorbable stent 530 of joint spacer 510 defines first and second poles 572A and 572B, which together define an axis 580 of bioresorbable stent 530. Typically, wires 260 cross one another within 3 mm of first pole 572A and within 3 mm of a second pole 572B when joint spacer 510 is unconstrained and bioresorbable stent 530 is in the expanded configuration. Optionally, anchor 322 is disposed at one of first and second poles 572A and 572B. Optionally, a central longitudinal axis of anchor 322 is coaxial with axis 580 of bioresorbable stent 530.

Bioresorbable stent 530 is disposed eccentrically about axis 580 when joint spacer 510 is unconstrained and bioresorbable stent 530 is in the expanded configuration. When joint spacer 510 is removably disposed in delivery tube 50 for delivery, joint spacer 510 is collapsed asymmetrically. For example, joint spacer 510 may be compressed on axis 580.

The scope of the present disclosure includes embodiments described in the following applications. In some embodiments, techniques and apparatus described in one or more of the following applications are combined with techniques and apparatus described herein:

U.S. Pat. No. 8,753,390 to Shohat
U.S. Pat. No. 8,894,713 to Shohat et al.
PCT Publication WO 2008/111073 to Shohat
PCT Publication WO 2010/097724 to Shohat
PCT Publication WO 2012/017438 to Shohat et al.
PCT Publication WO 2013/057566 to Shohat It will be appreciated by persons skilled in the art that the present disclosure is not limited to what has been particularly shown and described herein. Rather, the scope of the present disclosure includes both combinations and subcombinations of the various features described herein, as well as variations and modifications thereof that are not in the prior art, which would occur to persons skilled in the art upon reading the foregoing description.

What is claimed is:

1. An apparatus comprising a joint spacer for treatment of a joint of a human subject, the joint spacer comprising:
a bioresorbable structure having a plurality of struts defining a plurality of openings, the bioresorbable structure having compressed and expanded configurations; and
a covering that covers an external surface of the bioresorbable structure,
wherein the joint spacer is configured to be inserted into a space of the joint, and is shaped, when the bioresorbable structure is in the expanded configuration, to provide mechanical support to the joint until the bioresorbable structure resorbs into a body of the subject, wherein the covering is bioresorbable, the bioresorbable structure being configured to resorb into the body of the subject before the covering resorbs into the body of the subject.

2. The apparatus according to claim 1, wherein the covering is fluid-permeable and blood-permeable.

3. The apparatus according to claim 1, wherein the covering is tissue-permeable.

4. The apparatus according to claim 1, wherein the covering defines a non-tubular lumen therethrough when the joint spacer is unconstrained and the bioresorbable structure is in the expanded configuration, at least immediately upon placement within the joint.

5. The apparatus according to claim 1, wherein the covering is sachet-shaped at least immediately upon placement within the joint.

6. The apparatus according to claim 1, wherein the covering is rectangular at least immediately upon placement within the joint.

7. The apparatus according to claim 1, wherein the apparatus further comprises a delivery tube, in which the joint spacer is removably disposed for delivery in a radially-compressed configuration with a central longitudinal axis thereof parallel to a longitudinal axis of the delivery tube.

8. The apparatus according to claim 1, wherein the bioresorbable structure is a stent shaped generally as an elliptical cylinder, and wherein the length of the major axis of the elliptical cylinder equals at least 200% of the length of the minor axis of the elliptical cylinder when the bioresorbable structure is in the expanded configuration.

9. The apparatus according to claim 1, wherein the bioresorbable structure is configured to resorb into the body of the subject between 3 and 36 months after placement in the joint.

10. A method for treating a joint of a human subject, the method comprising:
inserting a joint spacer into a space of the joint while a bioresorbable structure of the joint spacer is in a compressed configuration, the bioresorbable structure having a plurality of struts defining a plurality of openings, wherein a covering of the joint spacer covers an external surface of the bioresorbable structure, the covering being bioresorbable and configured to absorb into a body of the subject after the bioresorbable structure absorbs into the body of the subject; and
transitioning the bioresorbable structure to an expanded configuration within the joint, such that the joint spacer provides mechanical support to the joint,
wherein the joint spacer is a subacromial spacer, and wherein inserting the joint spacer comprises inserting the subacromial spacer into a subacromial space of a shoulder joint.

11. The method according to claim 10, wherein the covering is shaped as a pouch within which the bioresorbable structure is disposed, at least immediately upon placement within the joint.

12. The method according to claim 10, wherein the bioresorbable structure is shaped as a partially-flattened tube when the joint spacer is unconstrained and the bioresorbable structure is in the expanded configuration.

13. The method according to claim 12, wherein inserting the joint spacer comprises inserting the joint spacer while it is removably disposed in a delivery tube in a radially-compressed configuration with a central longitudinal axis of the joint spacer parallel to a longitudinal axis of the delivery tube.

14. A method for treating a joint of a human subject, the method comprising:
inserting a joint spacer into a space of the joint while a bioresorbable structure of the joint spacer is in a compressed configuration, the bioresorbable structure having a plurality of struts defining a plurality of openings, wherein a covering of the joint spacer covers an external surface of the bioresorbable structure, the covering being bioresorbable and configured to absorb into a body of the subject after the bioresorbable structure absorbs into the body of the subject; and
transitioning the bioresorbable structure to an expanded configuration within the joint, such that the joint spacer provides mechanical support to the joint,
wherein the joint spacer is a glenohumeral spacer, and wherein inserting the joint spacer comprises inserting the glenohumeral spacer into a glenohumeral joint.

15. The method according to claim 14, wherein the covering is shaped as a pouch within which the bioresorbable structure is disposed, at least immediately upon placement within the joint.

16. The method according to claim 14, wherein the bioresorbable structure is shaped as a partially-flattened tube when the joint spacer is unconstrained and the bioresorbable structure is in the expanded configuration.

17. The method according to claim 16, wherein inserting the joint spacer comprises inserting the joint spacer while it is removably disposed in a delivery tube in a radially-compressed configuration with a central longitudinal axis of the joint spacer parallel to a longitudinal axis of the delivery tube.

* * * * *